United States Patent [19]

Frankhouser et al.

[11] 4,417,886
[45] Nov. 29, 1983

[54] CATHETER INTRODUCTION SET

[75] Inventors: Paul L. Frankhouser, Reading, Pa.; Ketan Shevde, Great Neck, N.Y.

[73] Assignee: Arrow International, Inc., Reading, Pa.

[21] Appl. No.: 318,469

[22] Filed: Nov. 5, 1981

[51] Int. Cl.³ .................. A61M 5/00; A61M 25/00
[52] U.S. Cl. ............................ 604/53; 604/164; 604/170; 128/658
[58] Field of Search ............... 128/214.4, 348–350, 128/DIG. 9, DIG. 16, 772, 658; 604/53, 164–170

[56] References Cited

U.S. PATENT DOCUMENTS

| | | | |
|---|---|---|---|
| 3,995,628 | 12/1976 | Gula | 128/214.4 |
| 4,068,659 | 1/1978 | Moorehead | 128/214.4 |
| 4,068,660 | 1/1978 | Beck | 128/214.4 |
| 4,205,675 | 6/1980 | Vaillancourt | 128/214.4 |
| 4,230,123 | 10/1980 | Hawkins | 128/772 X |
| 4,274,408 | 6/1981 | Nimrod | 128/214.4 |
| 4,306,562 | 12/1981 | Osborne | 128/214.4 |

Primary Examiner—Dalton L. Truluck
Attorney, Agent, or Firm—Charles H. Lindrooth

[57] ABSTRACT

Disclosed is a disposable introducer kit for the introduction of a catheter into small vessels such as the radial artery of a patient. The introducer assembly is contained in a sterile package and removed as an entire unit including needle, catheter, wire guide and wire guide feed device. The catheter is mounted on the introducer needle with the tip of the needle extending slightly beyond the tip of the catheter. A guide tube extends rearwardly from a hub on the back of the needle. The wire guide is mounted in the tube with a wire guide actuating handle projecting through an elongated slot in the side wall of the tubing. In use, the needle is first inserted into the lumen of the vessel. The spring wire guide is next advanced by means of the actuating handle as far as possible into the vessel. The catheter is then advanced forwardly to track the spring wire guide into the vessel to the desired position. Thereafter the spring wire guide, needle and feed tube assembly are all removed and the catheter connected to the desired equipment.

7 Claims, 4 Drawing Figures

U.S. Patent    Nov. 29, 1983    4,417,886
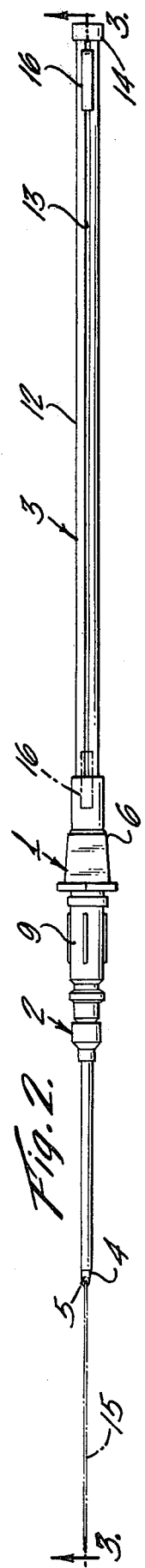
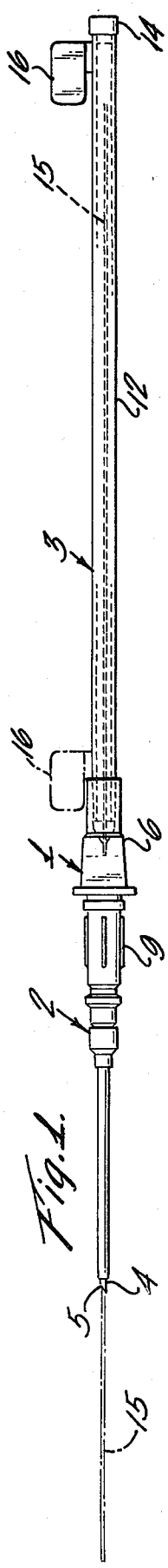
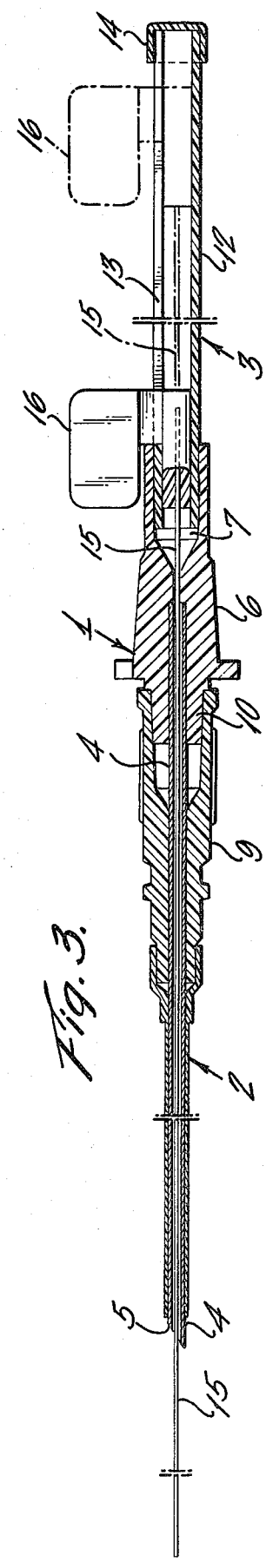
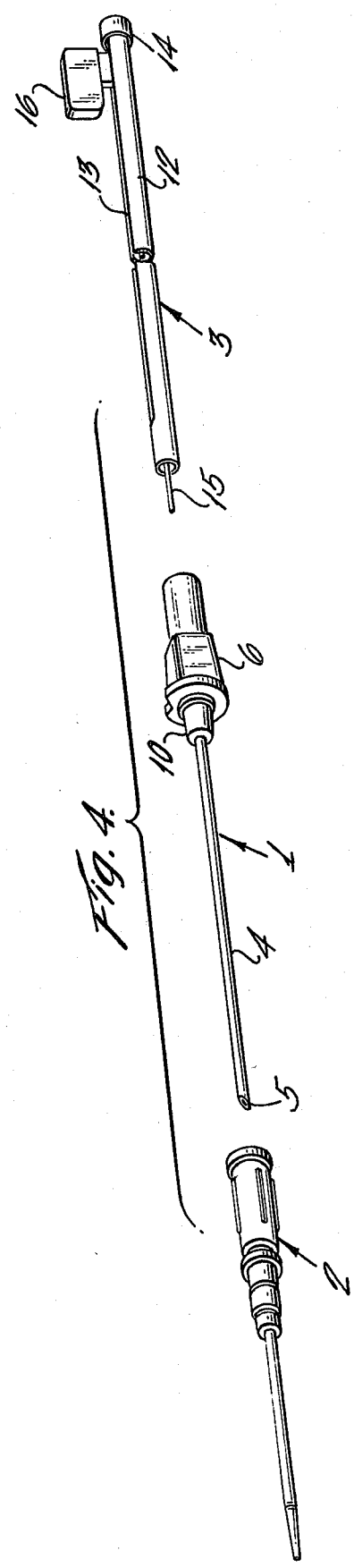

CATHETER INTRODUCTION SET

FIELD OF THE INVENTION

This invention relates to the introduction of catheters and more particularly to apparatus and method providing for improvements in reliability in the introduction of catheters into small diameter blood vessels.

BACKGROUND OF THE INVENTION

In accordance with the usual known prior art practice, in introducing a catheter into the lumen of a blood vessel, a hollow needle called an introducer needle is first inserted into the vessel. When the needle is properly positioned, a spring-wire guide is fed through the needle and advanced until the desired length of wire guide is within the vessel so as to provide a positive track for a catheter to follow. The catheter is threaded onto the guide and is advanced through the hollow needle until it is positioned as desired. The introducer needle and the wire guide are then removed from the patient.

Known prior art disclosing related techniques includes U.S. Pat. No. 4,068,659 and 4,068,660 both issued on Jan. 17, 1978. The '659 patent, discloses a cannulated needle sharpened at one end, having a connector at the other to which an elongated sheath is attached having a slit running lengthwise thereof. A flexible cannula or catheter is disposed within the sheath with its leading end resting within the hollow passage of the needle. The catheter is stiffened by a stylet of substantial rigidity which extends within the entire length of the catheter except for the tip thereof. The stylet has a handle projecting through the slot. The catheter is advanced through the needle into the vein by advancement of the handle. Once it is in place, the handle is retracted, leaving the catheter in place. Thereafter, the entire assembly, exclusive of the catheter, is withdrawn and discarded.

The arrangement disclosed in the '660 patent is similar except that the catheter has a spring wire helically wound tube on the proximal end. An adapter fitting is attached by twisting onto the helically wound part thereby deforming the wall and securely holding it in place.

SUMMARY OF THE INVENTION

In contrast to the foregoing, the present invention provides an assembly or kit which includes a small diameter cannulated introducer needle which fits within a catheter. The catheter has a hub at the proximal end which preferably includes a female Luer-type connector. The needle has a beveled tip projecting slightly beyond the end of the catheter. The proximal end of the needle has a hub formed of transparent material. A tubing formed of transparent plastic material extends rearwardly from the needle hub and contains a small diameter flexible spring wire guide. An actuating lever attached to the trailing end of the wire guide projects through a slit extending longitudinally of the tubing. The blood vessel is punctured by the needle, puncture being evidenced when arterial blood flashes back into the clear hub of the needle. The catheter and introducer needle are then held in position and the actuating lever of the spring wire guide is advanced toward the needle hub as far as possible via the slit in the clear plastic tubing. This action advances the spring wire guide through the lumen of the introducer needle into the blood vessel itself. The wire also acts as a stylet to inhibit subsequent back-bleeding through the needle while the soft tip aids in negotiating the blood vessel for a distance approximately equal to the length of the catheter to be inserted.

In the final step in use of the invention, the hub of the needle is held stationary and the catheter is advanced forwardly off of the needle into the blood vessel. The spring wire guide, being already in the vessel, provides a positive track for catheter advancement. Once the catheter is fully advanced, it is held in place and the introducer needle, the guide tube and wire guide removed and discarded. The catheter hub connector is then attached to its mating connector part, which part depends upon the intended use of the catheter.

OBJECTS AND ADVANTAGES OF THE INVENTION

An important object of the invention is the provision of a catheter introduction system which is particularly well suited for the introduction of catheters into relatively small diameter blood vessels such as a radial artery.

Another object of the invention is the provision of a catheter introduction apparatus and method in which both walls of small diameter blood vessels are not so readily transfixed, and if transfixed, the equipment and technique make it possible to easily guide the catheter into and through the vessel rather than through both walls of the vessel.

Another objective of the invention is the provision of equipment and techniques which reduce the likelihood that the catheter will be cut by the introducer needle as it is inserted into the blood vessel.

A still further object of the invention is the provision of equipment which permits use of smaller diameter introducer needles thereby facilitating puncture of small diameter blood vessels while still permitting the use of catheters having a relatively large internal diameter.

Still another objective of the invention is the provision of catheter introduction equipment which provides a simplified means of advancing a flexible spring wire guide into a small diameter blood vessel for catheter tracking purposes.

The various objects and advantages of the invention are achieved by a catheter introducer set including a cannulated introducer needle, a catheter sized to fit over the needle, an elongated tubular member connected to and projecting rearwardly from the proximal end of the needle with the passage through the needle being in communication with the interior of the tubular member, a flexible wire guide positioned within said tubular member and extending lengthwise thereof, the tubular member having a slot running lengthwise thereof, the wire guide having an actuating lever projecting through said slot and adapted to be manually advanced so as to move the wire guide through the needle and the lumen of the blood vessel thereby providing a guide track for positioning the catheter within the vessel. The wire guide, the needle and the tubular member are removed and discarded after placement of the catheter within the vessel.

Other objects and advantages of the invention will appear in the following detailed description of an illustrative embodiment of the invention in which:

FIGS. 1 and 2 are top and plan views respectively, showing a catheter introduction set formed in accordance with the teachings of the present invention;

FIG. 3 is a sectional view taken along line 3—3 of FIG. 2 but on a slightly enlarged scale with respect to FIG. 2; and FIG. 4 is a perspective exploded view, illustrating various features of the invention.

DETAILED DESCRIPTION OF THE INVENTION

As shown in the drawings, particularly in FIG. 4, the preferred form of the invention comprises in general, three separate portions, namely an introducer needle 1, a catheter 2 which fits over needle 1 and a wire guide assembly 3 which is secured at the rear of the needle portion 1 as will be described hereinafter. Needle 1 comprises an elongated shank portion 4 having a beveled tip 5. The shank is hollow or cannulated and is joined at its rear end to a hollow transparent hub 6 which is bored and counterbored for purposes to be explained hereinafter.

Catheter 2 is sized to be telescopically fitted over the shank of needle 1. The catheter is slightly shorter than the needle so that when it is fully pushed back against the needle hub 6 the beveled tip of the needle projects outwardly thereform by an amount sufficient to permit puncture of the blood vessel by the user of the device. Preferably a female Luer-type fitting 9 is formed on the rear of the catheter. In the position illustrated in FIGS. 1 through 3 the Luer-type female fitting 9 mates with and fits over a shouldered projection 10 on the front of hub 6.

The wire guide assembly 3 preferably comprises elongated tubular member 12 which is fitted into the counterbore 7 at the rear end of hub 6. Preferably, tubular member 12 is formed of a transparent, semi-rigid plastic material. Although the plastic material may have some flexibility it should have sufficient resilience so that it maintains its tubular configuration in use.

In its preferred form, tubular member 12 has a longitudinally extending slot 13 running from a point adjacent the needle hub 6. A plug 14 or other suitable sealing means provides a seal for the end.

An elongated, flexible spring wire guide 15 is housed within tubular member 12. Means for advancing the spring wire guide 15 preferably includes a laterally or radially extending handle 16 fastened to its rear end. Handle 16 projects through the slot 13 and is adapted to advance the spring wire guide through the lumen of needle 1 and outwardly from the distal end into and through the lumen of the blood vessel. Preferably, when the handle is in the retracted position shown in FIGS. 1 and 2, the tip of the wire guide sits just outside of the opening in the end of the needle. When the handle is advanced from the full line position shown in FIG. 1 to the position illustrated by broken lines in that figure (the full line position in FIG. 3) the distal end of the wire guide extends into the blood vessel the requisite amount needed to guide the catheter to its intended position.

In use, the entire introducer device as shown in FIGS. 1 through 3 is removed from a sterile package, not shown, and with all parts as shown in FIGS. 1 and 2, the selected blood vessel is punctured. In puncturing an artery for example, proper arterial puncture is evidenced when arterial blood "flows-back" into the clear hub 6 of needle 1. Catheter 2 and the introducer needle 1 are then held in position and the actuating handle 16 for the spring wire guide 15 is advanced toward the needle hub as far as possible. This motion advances the spring wire guide 15 through the lumen of the introducer needle into the lumen of the vessel. During this operation, the wire also acts as a stylet to inhibit back bleeding through the needle. The soft resilient tip of the wire guide safely and easily negotiates the vessel for a distance approximately equal to the length of the catheter to be inserted.

While holding the hub 6 stationary, the catheter is advanced forwardly off the needle and into the vessel. The spring wire guide, being already in the vessel, provides a positive track for catheter advancement. Once the catheter is fully advanced, it is manually held in place and the introducer needle with rear tube 12 and wire guide 15 is removed and discarded. The catheter hub is then attached to the mating connector of the equipment with which the catheter is intended to be used. If desired, a stopcock or injection cap may be fitted into the connector 9 until the catheter is ready for use.

The invention has been found to simplify the procedure of catherization of small blood vessels such as a radial artery. Usually the physician can effect proper placement of the catheter on the first try. The wire guide is easily manipulated by the handle 16 and readily follows the path of the artery. The over-the-needle catheter can then be quickly and easily advanced off the end of the needle and when the wire guide is removed the fitting on the catheter is ready to be connected to the equipment with which the catheter is to be used.

We claim:

1. A catheter introduction set for the introduction of a catheter into a relatively small diameter blood vessel comprising a hollow introducer needle having a beveled tip at the distal end, a catheter telescopically fitted over the needle, the needle and catheter being relatively dimensioned in length to expose the needle tip when the catheter is on the needle, an elongated tubular member connected to and projecting rearwardly from the proximal end of the needle, passage means providing communication between the hollow needle and the tubular member, an elongated flexible wire guide within said tubular member, means for advancing said flexible wire guide through the needle, said wire guide having a length substantially longer than the needle whereby the end of the wire guide enters the lumen of the blood vessel when the wire guide is advanced thereby providing a guide track for positioning the catheter within the vessel, and interconnecting means for the needle, the wire guide and the tubular member for separation thereof from the catheter for disposal once the catheter is in place in the blood vessel.

2. A catheter introduction set according to claim 1 wherein the means for advancing the wire guide comprises a slot extending lengthwise of the tubular member, an actuating handle on the proximal end of the wire guide extending outwardly through said slot, said lever being manually moveable so as to move the wire guide into and out of the vessel.

3. A catheter introduction set according to claim 1 wherein said tubular member is formed of a semi-rigid plastic material.

4. A catheter introduction set according to claim 3 wherein said introducer needle has an enlarged transparent hub at the proximal end thereof, said hub including a passageway in communication with the needle.

5. A catheter introduction set according to claim 4 wherein the distal end of said wire guide terminates just outside of said hub when the actuating handle is retracted and wherein said wire guide has a cross-sectional dimension relative to the cross-sectional dimension of the hollow needle sufficient to substantially restrict the flow of blood when the wire guide is advanced.

6. A catheter introduction set according to claim 5 wherein the proximal end of said catheter comprises a Luer-type connector.

7. A method of introduction of a catheter into a blood vessel of a patient comprising the steps of using a hollow introducer needle having a catheter telescopically fitted over the needle shank, the needle having a beveled tip which projects beyond the end of the catheter when the catheter is on the needle, wherein said needle has a tubular member extending rearwardly from the distal end thereof, an elongated flexible wire guide within the tubular member and means for advancing the wire guide through the hollow needle and outwardly through the needle tip, the method comprising: puncturing a selected blood vessel with the needle, thereafter while the needle tip is within the blood vessel, advancing the wire guide through the needle until a predetermined length is positioned within the blood vessel, thereafter advancing the catheter off the needle and over the wire guide until the catheter is placed within the vessel and then separating and withdrawing the needle, the tubular member and the wire guide from the positioned catheter.

* * * * *

REEXAMINATION CERTIFICATE (1398th)
United States Patent [19]
Frankhouser et al.

[11] B1 4,417,886
[45] Certificate Issued  Jan. 1, 1991

[54] CATHETER INTRODUCTION SET

[75] Inventors: Paul L. Frankhouser, Reading, Pa.; Ketan Shevde, Great Neck, N.Y.

[73] Assignee: Arrow International, Inc., Reading, Pa.

Reexamination Request:
No. 90/001,883, Nov. 1, 1989

Reexamination Certificate for:
Patent No.: 4,417,886
Issued: Nov. 29, 1983
Appl. No.: 318,469
Filed: Nov. 5, 1981

[51] Int. Cl.$^5$ .............................................. A61M 5/00
[52] U.S. Cl. ...................................... 604/53; 604/164; 604/170; 128/658
[58] Field of Search .......................... 604/53, 164–170, 604/284, 280; 128/658, 772

[56] References Cited

U.S. PATENT DOCUMENTS

| Number | Date | Name |
|---|---|---|
| Re. 27,797 | 10/1973 | Sorenson et al. |
| Re. 31,272 | 6/1983 | Pevsner |
| 1,147,408 | 7/1915 | Kells |
| 2,389,355 | 11/1945 | Goland et al. |
| 2,770,236 | 11/1956 | Utley et al. |
| 2,915,063 | 12/1959 | Cutter |
| 2,922,420 | 1/1960 | Cheng |
| 2,937,643 | 5/1960 | Elliot |
| 3,010453 | 11/1961 | Doherty |
| 3,013,559 | 12/1961 | Thomas |
| 3,055,361 | 9/1962 | Ballard |
| 3,097,646 | 7/1963 | Scislowicz |
| 3,185,151 | 5/1965 | Czorny |
| 3,204,634 | 9/1965 | Koehn |
| 3,219,036 | 11/1965 | Stafford |
| 3,220,411 | 11/1965 | Czorny |
| 3,225,762 | 12/1965 | Guttman |
| 3,262,448 | 7/1966 | Ring et al. |
| 3,312,220 | 4/1967 | Eisenberg |
| 3,313,299 | 4/1967 | Spademan |
| 3,335,723 | 8/1967 | Waldman, Jr. |
| 3,352,306 | 11/1967 | Hirsch |
| 3,382,872 | 4/1968 | Rubin |
| 3,459,183 | 8/1969 | Ring et al. |
| 3,459,184 | 8/1969 | Ring |
| 3,459,188 | 8/1969 | Roberts |
| 3,463,152 | 8/1969 | Sorenson |
| 3,500,828 | 3/1970 | Podhora |
| 3,503,385 | 3/1970 | Stevens |
| 3,515,137 | 6/1970 | Santomieri |
| 3,547,103 | 12/1970 | Cook |
| 3,547,119 | 12/1970 | Hall et al. |
| 3,561,445 | 2/1971 | Katerndahl et al. |
| 3,585,996 | 6/1971 | Reynolds et al. |
| 3,612,050 | 10/1971 | Sheridan |
| 3,670,729 | 6/1972 | Bennett et al. |
| 3,685,513 | 8/1972 | Bellamy, Jr. |
| 3,687,142 | 8/1972 | Leibinzohn |
| 3,703,174 | 11/1972 | Smith |
| 3,739,778 | 6/1973 | Monestere, Jr. et al. |
| 3,757,771 | 9/1973 | Ruegg et al. |
| 3,766,916 | 10/1973 | Moorehead et al. |
| 3,769,975 | 11/1973 | Nimoy et al. |
| 3,774,605 | 11/1973 | Jewett |
| 3,792,703 | 2/1974 | Moorehead |
| 3,809,081 | 5/1974 | Loveless |
| 3,811,440 | 5/1974 | Moorehead et al. |
| 3,825,001 | 7/1974 | Bennet et al. |
| 3,826,256 | 7/1974 | Smith |
| 3,833,003 | 9/1974 | Taricco |
| 3,835,854 | 9/1974 | Jewett |
| 3,851,647 | 12/1974 | Monestere, Jr. et al. |
| 3,856,009 | 12/1974 | Winnie |
| 3,856,010 | 12/1974 | Moorehead et al. |
| 3,903,885 | 9/1975 | Fuchs |
| 3,915,168 | 10/1975 | Monestere, Jr. et al. |
| 4,016,879 | 4/1977 | Mellor |
| 4,020,835 | 5/1977 | Nordstrom et al. |
| 4,033,331 | 7/1977 | Guss et al. |
| 4,037,599 | 7/1977 | Raulerson |
| 4,037,600 | 7/1977 | Poncy et al. |
| 4,046,144 | 9/1977 | McFarlane |
| 4,068,659 | 1/1978 | Moorehead |
| 4,073,297 | 2/1978 | Kopp |
| 4,099,528 | 7/1978 | Sorenson et al. |
| 4,149,535 | 4/1979 | Volder |
| 4,159,022 | 6/1979 | Peysner |
| 4,160,451 | 7/1979 | Chittenden |
| 4,217,895 | 8/1980 | Sagae et al. |
| 4,224,943 | 9/1980 | Johnson et al. |
| 4,230,123 | 10/1980 | Hawkins, Jr. |
| 4,235,232 | 11/1980 | Sparen et al. |
| 4,270,535 | 6/1981 | Bogue et al. |
| 4,274,408 | 6/1981 | Nimrod |
| 4,280,500 | 7/1981 | Ono |
| 4,280,503 | 7/1981 | Ackerman |
| 4,299,217 | 11/1981 | Sagae et al. |
| 4,311,137 | 1/1982 | Gerard |
| 4,326,520 | 4/1982 | Alley |
| 4,327,723 | 4/1982 | Frankhouser |
| 4,351,333 | 9/1982 | Lazarus et al. |
| 4,364,391 | 12/1982 | Toye |
| 4,479,792 | 10/1984 | Lazarus et al. |
| 4,496,348 | 1/1985 | Genese et al. |
| 4,553,960 | 11/1985 | Lazarus et al. |

FOREIGN PATENT DOCUMENTS

| | | |
|---|---|---|
| 2415196 | 10/1975 | Fed. Rep. of Germany |
| 49-5433 | 2/1974 | Japan |
| 55-14017 | 1/1980 | Japan |

OTHER PUBLICATIONS

"A Modified Instrument for Thoracentesis, Paracentesis and Intravenous Fluid Therapy", Eisenberg (1-1-7-63) N. Eng. J. Med. 268:143–144.

"Preliminary Communication–New Inventions", The Lancet, pp. 941–942 (Oct. 31, 1964).

"Catheters, Guides & Needles for the Percutaneous Technique", p. 29, USCI Catalog (1966).

"Cardiovascular Catheters & Accessories", USCI Catalog (1974).

Blitt, Casey D. et al., "Central Venous Catheterization via the External Jugular Vein", Journal of the American Medical Association, vol. 229, No. 7, pp. 817–818 (Aug., 1974).

Seldinger, Sven Ivar, "Catheter Replacement of the

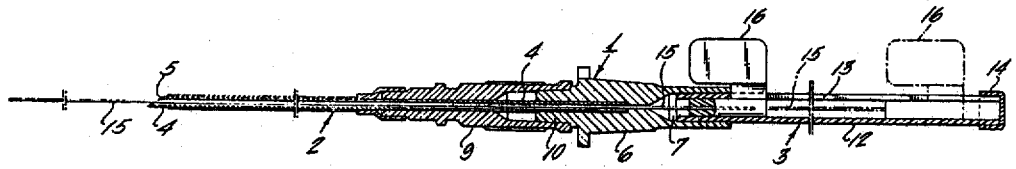

Needle in Percutaneous Arteriography", Acta Radiol 39:368–376 (1953).
Rosen; Michael et al., Handbook of Percutaneous Central Venous Catheterisation, pp. 115–120 (1981).
Verel, D. et al., "A Modified Seldinger Needle", Clin. Radiol. (1973) 24:65–66.

*Primary Examiner*—J. Yasko

[57] ABSTRACT

Disclosed is a disposable introducer kit for the introduction of a catheter into small vessels such as the radial artery of a patient. The introducer assembly is contained in a sterile package and removed as an entire unit including needle, catheter, wire guide and wire guide feed device. The catheter is mounted on the introducer needle with the tip of the needle extending slightly beyond the tip of the catheter. A guide tube extends rearwardly from a hub on the back of the needle. The wire guide is mounted in the tube with a wire guide actuating handle projecting through an elongated slot in the side wall of the tubing. In use, the needle is first inserted into the lumen of the vessel. The spring wire guide is next advanced by means of the actuating handle as far as possible into the vessel. The catheter is then advanced forwardly to track the spring wire guide into the vessel to the desired position. Thereafter the spring wire guide, needle and feed tube assembly are all removed and the catheter connected to the desired equipment.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1 and 3-7 is confirmed.

Claim 2 is determined to be patentable as amended.

2. A catheter introduction set according to claim 1 wherein the means for advancing the wire guide comprises a slot extending lengthwise of the tubular member, an actuating handle on the proximal end of the wire guide extending outwardly through said slot, said [lever] *actuating handle* being manually moveable so as to move the wire guide into and out of the vessel.

* * * * *